United States Patent [19]

Ahluwalia

[11] Patent Number: 5,095,007
[45] Date of Patent: Mar. 10, 1992

[54] ALTERATION OF RATE AND CHARACTER OF HAIR GROWTH

[76] Inventor: Gurpreet S. Ahluwalia, 8632 Stable View Ct., Gaithersburg, Md. 20879

[21] Appl. No.: 603,999

[22] Filed: Oct. 24, 1990

[51] Int. Cl.$^5$ ............................................. A61K 31/70
[52] U.S. Cl. ....................................................... 514/23
[58] Field of Search ......................................... 514/23

[56] References Cited

U.S. PATENT DOCUMENTS 4,720,480  1/1988  Shander ............................. 514/177
4,885,289 12/1989  Breuer et al. ....................... 514/177

OTHER PUBLICATIONS

Chem. Abst. 95-143848e (1981).
DeYoung et al., Cancer Research, 38:3697-3701 (1978).
Gale et al., "Alanosine and hadacidin—Comparison of effects on adenylosuccinate synthetase", Biochem. Pharmacology, vol. 17, 2495-2498 (1968).
Tyagi et al., "Studies on the mechanism of resistance of selected murine tumors to L-Alanosine", Biochem. Pharmacology, vol. 30, 915-924 (1981).
Tyagi et al., "Prospects for the chemotherapy of cancer using analogs of L-aspartic acid", TIPS, vol. 4, 299-304 (1983).

*Primary Examiner*—S. J. Friedman
*Attorney, Agent, or Firm*—Fish & Richardson

[57] ABSTRACT

The rate and character of mammalian hair growth is altered by the topical application to the skin of a composition containing an inhibitor of the enzymes adenylosuccinate synthetase or aspartate transcarbamylase.

10 Claims, No Drawings

ALTERATION OF RATE AND CHARACTER OF HAIR GROWTH

This invention relates to a method and composition for altering the rate and character of mammalian hair growth, particularly androgen-stimulated hair growth, by topical application to the skin of a composition containing an inhibitor of adenylosuccinate synthetase or of aspartate transcarbamylase.

BACKGROUND OF THE INVENTION

It has previously been proposed to alter the rate and character of hair growth by applying to the skin inhibitors of certain enzymes such as inhibitors of 5-alpha-reductase or of ornithine decarboxylase, or such antiandrogen materials as cytoplasmic androgen receptor binding agents, as described in U.S. Pat. Nos. 4,720,489 and 4,885,289. Moreover, it has been theorized that other enzymes, including gamma-glutamyl transpeptidase, are involved in various stages of hair follicle formation or of hair growth, but the relation between the various enzymes and the reactions which they control, as well as their effect upon each other and upon hair growth, has not been fully understood, as appears from Richards et al, Cancer Research, Vol. 42, 4143-4152 (1982); DeYoung et al, Cancer Research, Vol. 38, 3697-3701 (1978); and Chase, Physiolo. Zool., Vol. 24, 1-8 (1951).

It has now been found that the rate and character of mammalian (including human) hair growth, particularly androgen-stimulated hair growth, is altered by topical application to the skin of a composition containing an inhibitor of adenylosuccinate synthetase or of aspartate transcarbamylase.

Among the inhibitors of adenylosuccinate synthetase which may be used in the present invention are L-alanosine ([L-2-amino-3-(N-hydroxy, N-nitrosamino) propionic acid]), 6-mercaptopurine riboside 5'-phosphate, 8-aza guanosine monophosphate, 7-deaza-8-aza guanosine monophosphate, 2'-d guanosine monophosphate, $\beta$-D-arabinosyl guanosine monophosphate and the like. Inhibitors of aspartate transcarbamylase include N-phosphonacety -L-aspartic acid (PALA), 2-[[(phosphonomethyl) thio]methyl] succinic acid, O-phosphonoacetyl-L-malic acid, halogenated phosphonoacetyldioic or halogenated phosphonoacetyl aminodioic acids as described in European Patent Application 8,834 A, and bromosuccinate, among others. Of these, L-alanosine and PALA are preferred. It should be noted that L-alanosine is metabolically activated to L-alanosyl-5-amino-4-imidazole carboxylic acid ribonucleotide, which is formed in vivo and which is the direct or proximate inhibitor of the enzyme adenylosuccinate synthetase. L-alanosine is thus an indirect inhibitor of the enzyme but is included within the term inhibitor for the purpose of the present invention.

The composition of the present invention contains, in addition to the inhibitor, a non-toxic dermatologically acceptable vehicle or carrier which is adapted to be spread upon the skin. The concentration of the inhibitor in the composition may be varied over a wide range up to a saturated solution, preferably from 0.1 to 20% by weight or even more; the reduction of hair growth increases as the amount of inhibitor applied increases per unit area of skin. The maximum amount effectively applied is limited only by the rate at which the inhibitor penetrates the skin. Generally, the effective amounts range from 10 to 2500 micrograms or more per square centimeter of skin.

The following specific examples are intended to illustrate more clearly the nature of the present invention without acting as a limitation upon its scope.

EXAMPLE 1

A vehicle or carrier was prepared having the following composition:

| Component | Wt. Percent Concentration |
|---|---|
| Water | 68% |
| Ethanol | 16% |
| Propylene Glycol | 5% |
| Dipropylene Glycol | 5% |
| Benzyl Alcohol | 4% |
| Propylene Carbonate | 2% |

L-alanosine was mixed with separate portions of the foregoing vehicle to provide specimens containing 0.1, 0.5, 1, 2, and 6% by weight respectively of the inhibitor and the pH was adjusted to pH 7.5 with sodium hydroxide.

Four groups (eight animals in each group) of male intact Golden Syrian hamsters were provided. These animals were considered acceptable models for human beard hair growth in that they display oval shaped flank organs, one on each side, each about 8 mm. in major diameter, which grow thick black and coarse hair similar to human beard hair. These organs produce hair in response to androgens in the hamster. The flank organs of each hamster were depilated by applying a thioglycolat-- based chemical depilatory (Surgex), and to one organ of each animal was applied 10-25 $\mu$l. of vehicle alone once a day, while to the other organ of each animal was applied an equal amount of vehicle containing inhibitor. After three weeks of such applications (five days a week), the flank organs were shaved and the amount of recovered hair (hair mass) from each was weighed. The extent of reduction in hair growth by the inhibitor was expressed as the percent decrease in hair mass on the organ treated with inhibitor as compared to the organ treated with vehicle alone. As a control, one group of eight animals had both flank organs of each animal treated with vehicle alone. The results were as shown in Table 1 below.

TABLE 1

Inhibition of Hair Growth by L-alanosine
Hamster Flank Organ Hair Mass (mg)

| Treatment Group | Formulation Amount | Concentration of the Active | Untreated (mean) | Treated (mean) | Percent Inhibition |
|---|---|---|---|---|---|
| Control | 25 $\mu$l | — | 0.58 | 0.61 | — |
| L-alanosine | 25 $\mu$l | 0.1% | 0.83 | 0.68 | 18% |
| L-alanosine | 25 $\mu$l | 0.5% | 0.98 | 0.67 | 32% |
| L-alanosine | 25 $\mu$l | 1.0% | 0.71 | 0.38 | 47% |
| L-alanosine | 25 $\mu$l | 2.0% | 1.32 | 0.51 | 61% |

TABLE 1-continued

Inhibition of Hair Growth by L-alanosine
Hamster Flank Organ Hair Mass (mg)

| Treatment Group | Formulation Amount | Concentration of the Active | Untreated (mean) | Treated (mean) | Percent Inhibition |
|---|---|---|---|---|---|
| L-alanosine | 25 μl | 6.0% | 0.93 | 0.07 | 92% |

The hair on the treated organ was also observed to be more vellous in nature than that on the untreated organ.

In addition, it was found that similar topical treatments with a 10% solution of L-alanosine, twice over a 24 hour period, resulted in about 49% inhibition of adenylosuccinate synthetase activity in the hamster hair follicles.

The effect of the enzyme inhibition, was further shown by measurements of hair follicle nucleotide levels after topical treatment with L-alanosine. A group of eight hamsters was treated topically with L-alanosine (10% in the vehicle above) on one flank organ while the other organ received an equal amount of just the vehicle. After three days of daily treatments, the hair follicles from the flank organs were removed and the adenosine nucleotide contents were determined. L-alanosine treatment caused reduction in AMP, ADP, and ATP levels in hair follicles by 50, 40 and 29%, respectively.

EXAMPLE 2

A series of compositions was prepared containing various percentages by weight of N-phosphonacetyl-L-aspartic acid (PALA) in the vehicle described in Example 1 above adjusted to pH 4.5, and applied to hamster flank organs under the same conditions as described in Example 1. The reduction in hair growth observed after three weeks was as follows:

TABLE 2

INHIBITION OF HAIR GROWTH BY PALA
HAMSTER FLANK ORGAN HAIR MASS (mg)

| Treatment Group | Formulation Amount | Concentration of the active | Untreated Mean | Treated Mean | Percent Inhibition |
|---|---|---|---|---|---|
| Control | 25 μl | — | 1.79 | 1.76 | — |
| PALA | 25 μl | 2% | 1.66 | 1.34 | 19% |
| PALA | 25 μl | 4% | 1.69 | 0.85 | 50% |
| PALA | 25 μl | 6% | 1.73 | 0.23 | 87% |
| PALA | 10 μl | 2% | 1.56 | 1.36 | 13% |
| PALA | 10 μl | 6% | 1.67 | 0.37 | 78% |

It was found that similar topical treatments with a 10% solution of PALA (two treatments with a 10% solution of PALA (over a 24 hour period) resulted in a 72% reduction of aspartate transcarbamylase activity in the hamster hair follicles.

The effect of PALA administration on pyrimidine nucleotide content of hair follicles was determined, using the same treatment protocol as for determining nucleotide content in Example 1. the results were inhibition of UDP by 25%, UTP by 50%, CDP by 19%, and CTP by 60%.

What is claimed is:

1. The process of reducing the rate and altering the character of mammalian hair growth which comprises the step of applying to the skin an amount which is an effective dose of a composition containing an inhibitor of adenylosuccinate synthetase.

2. The process as claimed in claim 1 in which said inhibitor is L-alanosine.

3. The process as claimed in claim 1 or claim 2 in which the rate of applying is from 10 to 2500 micrograms of said inhibitor per square centimeter of skin.

4. The process of reducing the rate and altering the character of mammalian hair growth which comprises the step of applying to the skin an amount which is an effective dose of a composition containing an inhibitor of aspartate transcarbamylase.

5. The process as claimed in claim 4 in which said inhibitor is N-phosphonacetyl-L-aspartic acid.

6. The process as claimed in claim 1 or claim 2 in which the rate of applying is from 10 to 2,500 micrograms of said inhibitor per square centimeter of skin.

7. A topical composition for reducing the rate and altering the character of mammalian hair growth comprising a non-toxic dermatologically acceptable vehicle and from 0.1 to 20%, based on the total weight of said composition, of an inhibitor of adenylosuccinate synthetase, wherein said vehicle has the following composition:

| Component | Wt. Percent Concentration |
|---|---|
| Water | 68% |
| Ethanol | 16% |
| Propylene Glycol | 5% |
| Dipropylene Glycol | 5% |
| Benzyl Alcohol | 4% |
| Propylene Carbonate | 2% |

8. A composition as claimed in claim 7 in which said inhibitor is L-alanosine.

9. A topical composition for reducing the rate and altering the character of mammalian hair growth comprising a non-toxic dermatologically acceptable vehicle and from 0.1 to 20%, based on the total weight of said composition, of an inhibitor of aspartate transcarbamylase, wherein said vehicle has the following composition:

| Component | Wt. Percent Concentration |
|---|---|
| Water | 68% |
| Ethanol | 16% |
| Propylene Glycol | 5% |
| Dipropylene Glycol | 5% |
| Benzyl Alcohol | 4% |
| Propylene Carbonate | 2% |

10. A composition as claimed in claim 9 in which said inhibitor is N-phosphonacetyl-L-aspartic acid.

* * * * *

UNITED STATES PATENT AND TRADEMARK OFFICE
CERTIFICATE OF CORRECTION

PATENT NO. : 5,095,007

DATED : March 10, 1992

INVENTOR(S) : Gurpreet S. Ahluwalia

It is certified that error appears in the above-identified patent and that said Letters Patent is hereby corrected as shown below:

```
     Col. 1, line 44, "phosphonacety" should be
--phosphonacetyl--.
     Col. 1, line 49, "8,834" should be --328,834--
     Col. 4, line 12, delete "the" before "skin".
```

Signed and Sealed this

Tenth Day of August, 1993

Attest:

MICHAEL K. KIRK

*Attesting Officer*     *Acting Commissioner of Patents and Trademarks*